United States Patent
Policello et al.

(10) Patent No.: US 10,542,746 B2
(45) Date of Patent: Jan. 28, 2020

(54) LECITHIN-BASED SPRAY ADJUVANT CONTAINING ORGANOSILICON WETTING AGENTS

(71) Applicant: Momentive Performance Materials Inc., Waterford, NY (US)

(72) Inventors: George A Policello, Ossining, NY (US); Jeferson A Naue, Yorktown Heights, NY (US); Mary Ann Paccione, West Haverstraw, NY (US); Fengqi He, Shanghai (CN); Narayan Mukherjee, Croton-on-Hudson, NY (US)

(73) Assignee: Momentive Performance Materials Inc., Waterford, NY (US)

( * ) Notice: Subject to any disclaimer, the term of this patent is extended or adjusted under 35 U.S.C. 154(b) by 0 days.

(21) Appl. No.: 15/468,350

(22) Filed: Mar. 24, 2017

(65) Prior Publication Data

US 2017/0280713 A1    Oct. 5, 2017

Related U.S. Application Data (60) Provisional application No. 62/316,183, filed on Mar. 31, 2016.

(51) Int. Cl.
*A01N 25/30* (2006.01)
*A01N 25/24* (2006.01)
*A01N 39/04* (2006.01)
*A01N 57/12* (2006.01)

(52) U.S. Cl.
CPC ............. *A01N 25/30* (2013.01); *A01N 25/24* (2013.01); *A01N 39/04* (2013.01); *A01N 57/12* (2013.01)

(58) Field of Classification Search
CPC ........ A01N 25/30; A01N 25/24; A01N 39/04; A01N 57/12
See application file for complete search history.

(56) References Cited

U.S. PATENT DOCUMENTS

| | | | |
|---|---|---|---|
| 3,159,601 A | 12/1964 | Ashby | |
| 3,220,972 A | 11/1965 | Lamoreaux | |
| 3,715,334 A | 2/1973 | Karstedt | |
| 3,775,452 A | 11/1973 | Karstedt | |
| 3,814,730 A | 6/1974 | Karstedt | |
| 5,430,167 A | 7/1995 | Klein et al. | |
| 5,558,806 A | 9/1996 | Policello et al. | |
| 5,674,832 A | 10/1997 | Keys | |
| 6,130,186 A | 10/2000 | Ward et al. | |
| 6,797,673 B1 | 9/2004 | Worthley et al. | |
| 7,507,775 B2 | 3/2009 | Leatherman et al. | |
| 7,645,720 B2 | 1/2010 | Leatherman et al. | |
| 7,652,072 B2 | 1/2010 | Leatherman et al. | |
| 7,700,797 B2 | 4/2010 | Leatherman et al. | |
| 7,879,916 B2 | 2/2011 | Leatherman et al. | |
| 7,935,842 B2 | 5/2011 | Policello et al. | |
| 8,809,234 B1 | 8/2014 | Parrish | |
| 9,034,960 B2 | 5/2015 | Brown et al. | |
| 2007/0269467 A1 | 11/2007 | Leatherman et al. | |
| 2011/0105428 A1 | 5/2011 | Leatherman et al. | |
| 2014/0031467 A1 | 1/2014 | Brown et al. | |
| 2015/0057157 A1* | 2/2015 | Baseeth | A01N 25/04 504/363 |
| 2015/0237851 A1 | 8/2015 | Drew | |
| 2015/0245606 A1 | 9/2015 | Drew | |

FOREIGN PATENT DOCUMENTS

| | | |
|---|---|---|
| CN | 102396449 A | 7/2013 |
| EP | 0710500 B1 | 11/2000 |
| WO | 9817112 A1 | 4/1998 |
| WO | 2007139615 A2 | 6/2007 |
| WO | 2007127016 A1 | 11/2007 |
| WO | 2008073396 A1 | 6/2008 |
| WO | 2008073397 A1 | 6/2008 |
| WO | 2014018070 A1 | 1/2014 |

OTHER PUBLICATIONS

Business Wire, Momentive Performance Materials Introduces Next Generation Silwet* Adjuvants for Agricultural Applications, published: Aug. 6, 2007.*
International Search Report and Written Opinion from PCT/US2017/024038 dated May 31, 2017.

\* cited by examiner

*Primary Examiner* — Johann R Richter
*Assistant Examiner* — Genevieve S Alley
(74) *Attorney, Agent, or Firm* — Joseph S. Ostroff (57) ABSTRACT

An adjuvant composition contains lecithin and an organosilicon surfactant as defined herein.

16 Claims, 5 Drawing Sheets

Figure 1:
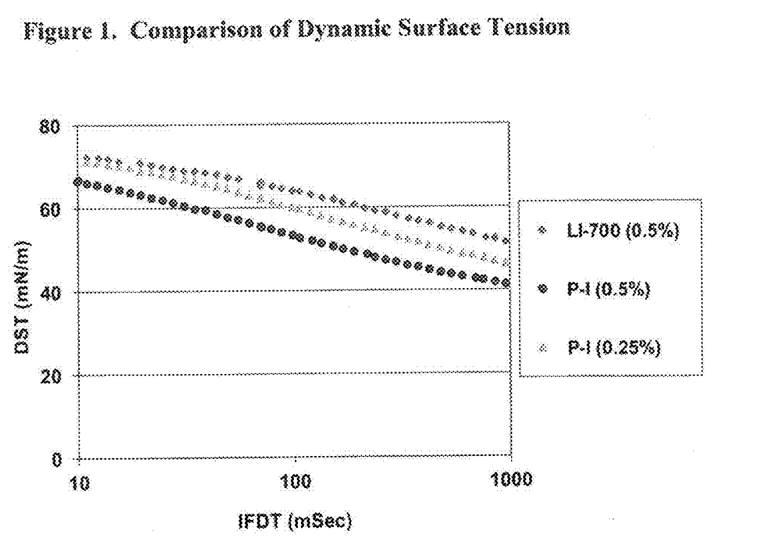

Figure 1. Comparison of Dynamic Surface Tension

Figure 2:
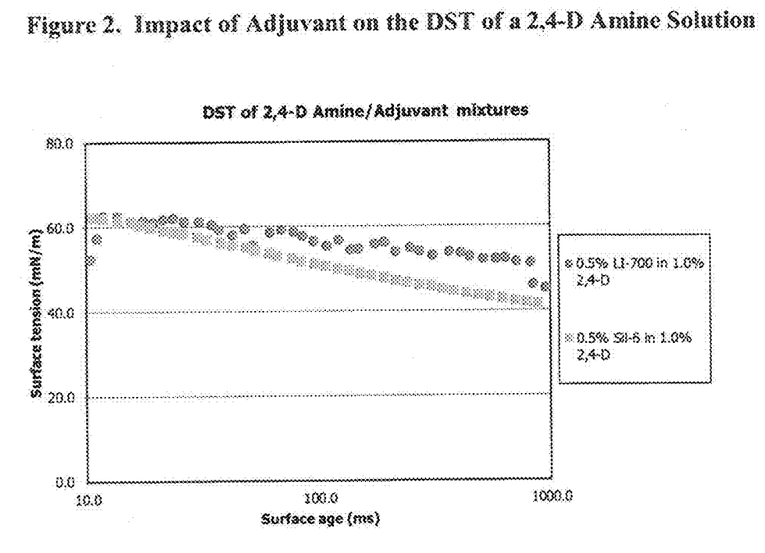

Figure 2. Impact of Adjuvant on the DST of a 2,4-D Amine Solution

Figure 3:
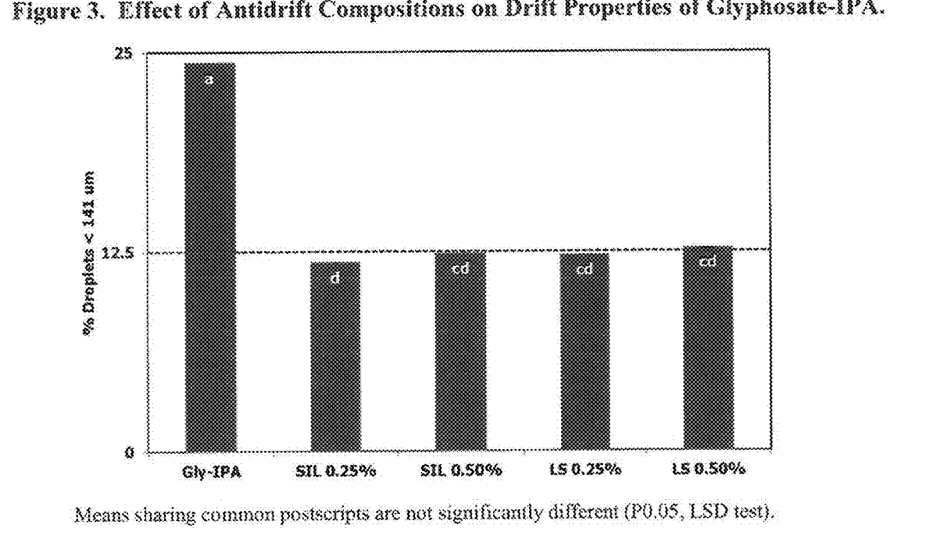

Figure 3. Effect of Antidrift Compositions on Drift Properties of Glyphosate-IPA.

Means sharing common postscripts are not significantly different (P0.05, LSD test).

Figure 4:
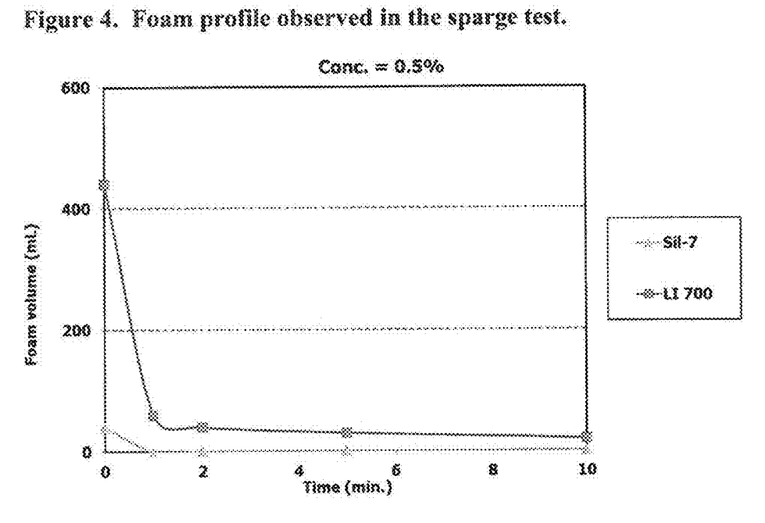

Figure 4. Foam profile observed in the sparge test.

Figure 5:
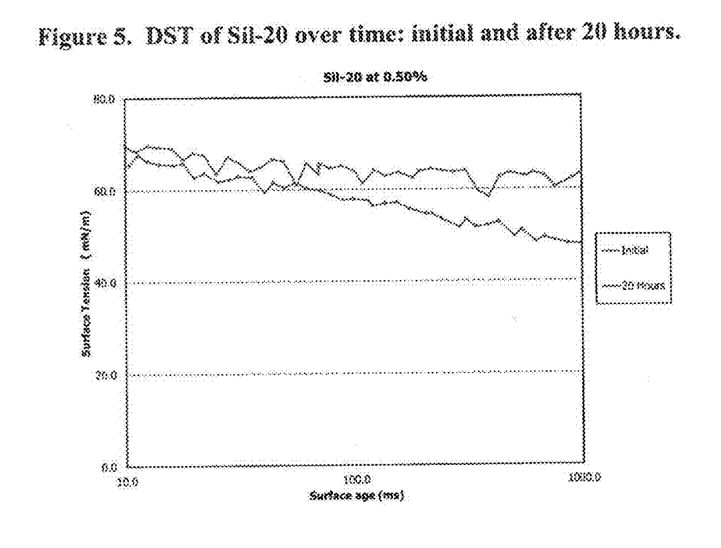

Figure 5. DST of Sil-20 over time: initial and after 20 hours.

Figure 6:
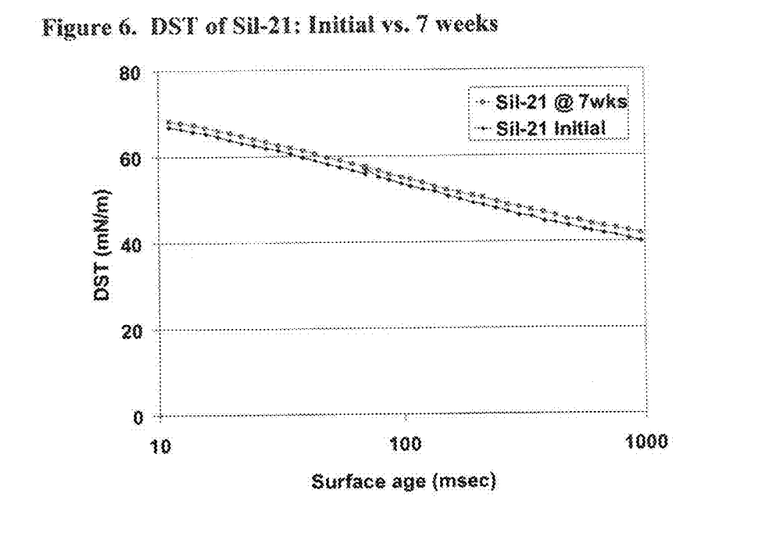

Figure 6. DST of Sil-21: Initial vs. 7 weeks

Figure 7:
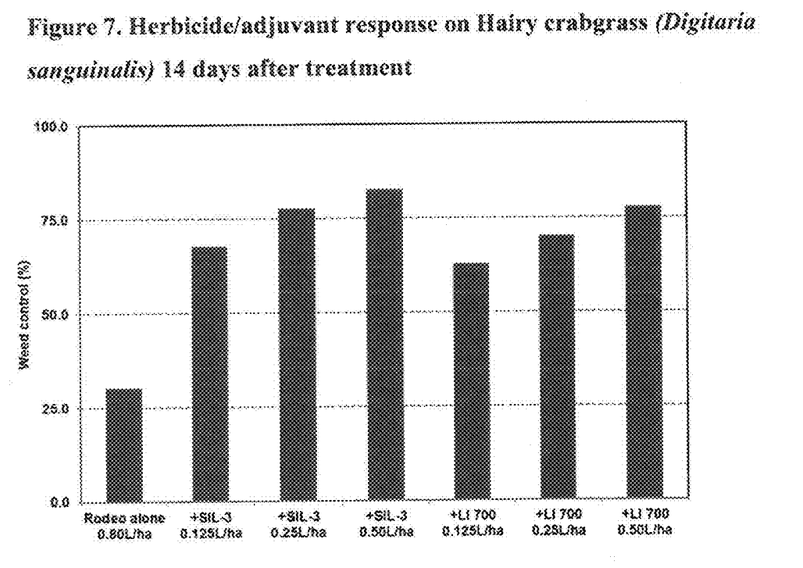

Figure 7. Herbicide/adjuvant response on Hairy crabgrass *(Digitaria sanguinalis)* 14 days after treatment Figure 8. Herbicide/adjuvant response on Smooth crabgrass *(Digitaria ischaemum)* 14 days after treatment Figure 9. Herbicide/adjuvant response on crabgrass Ribwort Plantain (*Plantago lanceolate*) 14 days after treatment

LECITHIN-BASED SPRAY ADJUVANT CONTAINING ORGANOSILICON WETTING AGENTS

CROSS REFERENCE TO RELATED APPLICATION

This application claims the benefit of U.S. provisional patent application Ser. No. 62/316,183, filed Mar. 31, 2016, the entire contents of which are incorporated by reference herein.

FIELD OF THE INVENTION

This invention relates to adjuvant compositions for agrochemical formulations and more particularly to such adjuvants containing lecithin and a surfactant.

Agrochemicals, e.g., those formulated as pesticides, plant growth regulators, fertilizers, and the like, in addition to their bioactive component(s), may also include one or more adjuvants, e.g., an antidrift, or spray drift, inhibitor such as lecithin to minimize the spread of the spray beyond its intended target area, and one or more surfactants, e.g., nonionic surfactants, for enhancing or increasing deposition and/or retention of spray droplets upon external plant tissue surfaces, penetration of the bioactive component(s) into internal plant structures, uptake of bioactive component(s) by the plant and/or for water conditioning.

Surfactants exhibiting superior performance for one or more of these functional capabilities continues to be an object of investigation within the agrochemical industry and its suppliers. Surfactants demonstrating even a modest improvement over known surfactants for just one of these capabilities, much less for two or more of them, would be highly desirable for the formulation of lecithin-based antidrift adjuvants which because of their widespread and high volume of use offer significant economies for their users.

SUMMARY OF THE INVENTION

In accordance with the present invention, there is provided an adjuvant composition for an agrochemical formulation comprising:

a) lecithin; and, b) organosilicon surfactant of general formula (I):

$$R^1—Si(R^2)(R^3)—Z \qquad (I)$$

wherein:

$R^1$ is a linear or branched monovalent hydrocarbon group of from 1 to 8 carbon atoms or a $R^4—Si(R^5)(R^6)—R^7—$ group in which $R^4$ is a linear or branched monovalent hydrocarbon group of from 1 to 8 carbon atoms, $R^5$ and $R^6$ are independently a linear or branched monovalent hydrocarbon group of from 1 to 4 carbon atoms and $R^7$ is a linear or branched divalent hydrocarbon group of from 1 to 4 carbon atoms;

$R^2$ and $R^3$ are independently a linear or branched monovalent hydrocarbon group of from 1 to 4 carbon atoms; and, Z is an alkylene oxide-containing group of up to 15 alkylene oxide units with each unit independently containing from 1 to 4 carbon atoms; a cationic group or a quaternary group free of alkyl halide.

Agrochemical formulations for application to plants as sprays and containing an adjuvant composition comprising lecithin and one or more organosilicon surfactant(s) (I) have been found to demonstrate superior performance for one or more of the functional properties stated above, e.g., more effective antidrift performance, superior deposition and/or retention of spray droplets upon plant surfaces such as leaves and stems, faster and/or deeper penetration of spray bioactive(s) into internal plant tissues resulting in faster and/or greater uptake of such bioactive(s) by the plant, and improved water conditioning. Thus, e.g., the adjuvant composition of the invention allows less such composition to be used for an equal antidrift effect, or the same amount for a faster and/or greater antidrift effect, than lecithin-based antidrift compositions formulated with conventional or otherwise known surfactants.

BRIEF DESCRIPTION OF THE DRAWINGS

FIG. 1 is a graphical presentation of experimental data comparing the dynamic surface tension (DST) properties of several antidrift compositions.

FIG. 2 is a graphical presentation of data showing the impact of several antidrift compositions on the DST of a 2,4-D amine solution.

FIG. 3 is a graphical presentation of data showing the effect of several antidrift compositions on the drift properties of glyphosate-IPA solutions.

FIG. 4 is a graphical comparison of foam control data for several antidrift compositions.

FIG. 5 is a graphical comparison of DST measurements taken initially and at 20 hours of an antidrift composition prepared with a trisiloxane alkoxylates surfactant.

FIG. 6 is a graphical comparison of DST measurements taken initially and at 7 weeks storage of an antidrift composition in accordance with the invention.

FIGS. 7, 8 and 9 are graphical comparisons of the effects of various adjuvant compositions in accordance with this invention on the responses of, respectively, hairy crabgrass (*Digitaria sanquinalis*), smooth crabgrass (*Digitaria ischaemum*) and ribwort plantain (*Plantago lanceolate*), to application of the herbicide Rodeo (glyphosate).

DETAILED DESCRIPTION OF THE INVENTION

In the specification and claims herein, the following terms and expressions are to be understood as indicated.

The singular forms "a," "an," and "the" include the plural, and reference to a particular numerical value includes at least that particular value, unless the context clearly dictates otherwise.

All methods described herein may be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed.

No language in the specification should be construed as indicating any non-claimed element as essential to the practice of the invention.

The terms, "comprising," "including," "containing," "characterized by," and grammatical equivalents thereof are inclusive or open-ended terms that do not exclude additional, unrecited elements or method steps, but will also be understood to include the more restrictive terms "consisting of" and "consisting essentially of."

It will be understood that any numerical range recited herein includes all sub-ranges within that range and any combination of the various endpoints of such ranges or sub-ranges.

It will be further understood that any compound, material or substance which is expressly or implicitly disclosed in the specification and/or recited in a claim as belonging to a group of structurally, compositionally and/or functionally related compounds, materials or substances includes individual representatives of the group and all combinations thereof.

The term "adjuvant" means any composition, material or substance which increases the efficacy of a bioactive material. The expressions "antidrift adjuvant" and "antidrift composition" are used synonymously herein.

The term "bioactive" refers to an agricultural chemical or material, including but not limited to pesticides, e.g., herbicides, fungicides, insecticides, acaricides and molluscides; plant nutrients; defoliants; and, plant growth regulators.

The term "lecithin" refers to a composition comprising one or more types of phospholipids, including but not limited to, phosphatidylcholine, phosphatidylethanolamine, phosphatidylserine and phosphatidylinositol. Lecithin may be derived from sources including, but not limited to, soy, safflower, sunflower and rapeseed.

The term "surfactant" means any compound that lowers the surface tension of a liquid, the interfacial tension between two liquids or the tension between a liquid and a solid.

As used herein, the term "water conditioning" means the property of increasing the solubility of a bioactive material, e.g., an herbicide, in water and/or binding to ions in water including but not limited to cations in hard water.

The expression "hydrocarbon group" means any hydrocarbon from which one or more hydrogen atoms has been removed, and is inclusive of alkyl, alkenyl, alkynyl, cyclic alkyl, cyclic alkenyl, cyclic alkynyl, aryl, aralkyl and arenyl groups and is inclusive of hydrocarbon groups containing at least one heteroatom.

The term "alkyl" means any monovalent, saturated straight, branched or cyclic hydrocarbon group; the term "alkenyl" means any monovalent straight, branched, or cyclic hydrocarbon group containing one or more carbon-carbon double bonds where the site of attachment of the group can be either at a carbon-carbon double bond or elsewhere therein; and, the term "alkynyl" means any monovalent straight, branched, or cyclic hydrocarbon group containing one or more carbon-carbon triple bonds and, optionally, one or more carbon-carbon double bonds, where the site of attachment of the group can be either at a carbon-carbon triple bond, a carbon-carbon double bond or elsewhere therein. Examples of alkyls include methyl, ethyl, propyl and isobutyl. Examples of alkenyls include vinyl, propenyl, allyl, methallyl, ethylidenyl norbornane, ethylidene norbornyl, ethylidenyl norbomene and ethylidene norbornenyl. Examples of alkynyls include acetylenyl, propargyl and methylacetylenyl, The expressions "cyclic alkyl", "cyclic alkenyl", and "cyclic alkynyl" include bicyclic, tricyclic and higher cyclic structures as well as the aforementioned cyclic structures further substituted with alkyl, alkenyl, and/or alkynyl groups. Representative examples include norbornyl, norbornenyl, ethylnorbonyl, ethylnorbornenyl, cyclohexyl, ethylcyclohexyl, ethyleyclohexenyl, cyclohexylcyclohexyl and cyclododecatrienyl.

The term "aryl" means any monovalent aromatic hydrocarbon group; the term "aralkyl" means any alkyl group (as defined herein) in which one or more hydrogen atoms have been substituted by the same number of like and/or different aryl (as defined herein) groups; and, the term "arenyl" means any aryl group (as defined herein) in which one or more hydrogen atoms have been substituted by the same number of like and/or different alkyl groups (as defined herein). Examples of aryls include phenyl and naphthalenyl. Examples of aralkyls include benzyl and phenethyl. Examples of arenyls include tolyl and xylyl.

The term "hetroatom" means any of the Group 13-17 elements except carbon and includes, for example, oxygen, nitrogen, silicon, sulfur, phosphorus, fluorine, chlorine, bromine and iodine.

The term "superspreader" as applied to organosilocone surfactants (I) herein refers to the property of "superspreading" or "superwetting". Superspreading/superwetting is the ability of a drop of a solution of surpersreader surfactant to spread to a diameter that is greater than the diameter of a drop of distilled water on a hydrophobic surface, and also greater than the diameter to which a solution of water and non-superspreading surfactant spreads, on the hydrophobic surface. In addition to this difference in spread diameter, the contact angle of a drop of superspreader surfactant solution on a surface is <5° and therefore smaller than that of a non-superspreading surfactant solution on the same surface.

A. Lecithin

In one embodiment of the adjuvant composition herein, its lecithin component may contain from 10 to 70 weight percent lecithin as phosphalidylcholine (PC) with the balance selected from phosphalidyletholamine (PE), phosphalidylinositol (PI) and phosphatidic acid (PA), and having an average acetone insoluble (AI) content of more than 60 weight percent.

The lecithin may be derived from egg or one or more vegetable sources such as soy, safflower, sunflower, rapeseed, and the like. Non-limiting examples of useful lecithins include the Alcolec® lecithins, e.g., Alcolec® F-100, Alcolec® SGV, Alcolec® SGB, Alcolec® S and Alcolec® XTRA-A from American Lecithin Company; Yelkin® and Ultralec® lecithins, e.g., Yelkin® SS, Yelkin® TS and Ultralec® F from Archer Daniels Midland Company; and, the Topcithin™, Leciprime™ and Lecisoy™ lecithins from Cargill, incorporated.

Lecithin whatever its composition or source will be present in the antidrift composition in at least a drift-reducing or drift-inhibiting effective amount, i.e., in at least an antidrift-effective amount, such as from 1 to 80, preferably from 10 to 70 and more preferably from 10 to 50, weight percent based on the total weight of lecithin and silicone surfactant (I).

B. Organosilicon Surfactant (I)

The organosilicon surfactant component of the adjuvant composition herein is represented by formula (I)

$$R^1\text{—}Si(R^2)(R^3)\text{—}Z \tag{I}$$

wherein:

$R^1$ is a linear or branched monovalent hydrocarbon group of from 1 to 8 carbon atoms such as methyl, ethyl, propyl, isopropyl, n-butyl, s-butyl, t-butyl, pentyl, isopentyl, hexyl, isohexyl, octyl, n-octyl, and the like, and is preferably methyl, ethyl, propyl, isopropyl, n-buytyl, s-butyl or t-butyl, or $R^1$ is an $R^4$—$Si(R^5)(R^6)$—$R^7$ group in which $R^4$ is a linear or branched monovalent group of 1 to 8 carbon atoms, e.g., any of those indicated above for $R^1$ and preferably methyl, ethyl, propyl, isopropyl, n-butyl, s-butyl or t-butyl, $R^5$ and $R^6$ are independently a linear or branched monovalent hydrocarbon group of 1 to 4 carbon atoms such as methyl, ethyl, propyl, isopropyl, n-butyl, s, butyl or t-butyl and are preferably methyl, ethyl, propyl or isopropyl, $R^7$ is a linear or branched chain divalent hydrocarbon group of from 1 to 4 carbon atoms such as methylene, ethylene, propylene, 1-methylethylene, 2-methylethylene, butylene, 1-methylpropylene, 2-methylpropylene or 3-methylpropylene and is preferably methylene or propylene;

$R^2$ and $R^3$ are independently a linear or branched monovalent hydrocarbon group of from 1 to 4 carbon atoms such as methyl, ethyl, propyl, isopropyl, n-butyl, s-butyl or t-butyl and are preferably methyl, ethyl, propyl or isopropyl; and, Z is an alkylene oxide-containing group of from 1 to 15, more specifically from 3 to 12 and still more specifically from 5 to 12, alkylene oxide units in which each alkylene oxide unit independently contains from 1 to 4 carbon atoms, or Z is a cationic group or a quaternary group free of alkylhalide.

Z may therefore be represented by general formula:

$$-R^8O[(C_2H_4O)_a(C_3H_6O)_b(C_4H_8O)_c]_d-R^9$$

wherein:

$R^8$ is a linear or branched divalent hydrocarbon group of from 3 to 8 carbon atoms, and preferably from 3 to 6 carbon atoms, e.g., propylene, isopropylene, n-butylene, isobutylene, pentylene, isopentylene, hexylene, isohexylene, and the like; $R^9$ is hydrogen, a monovalent hydrocarbon radical of from 1 to 4 carbon atoms such as any of those aforementioned, $R^A$—$N^{\oplus}(R^{10})(R^{11})R^{12}X^{\ominus}$, $R^B$—$N^{\oplus}(R^{13})(R^{14})R^{15}X^{\ominus}$ or $R^B$—$N^{\oplus}(R^{13})(R^{14})R^{15}X^{\ominus}$ in which $R^A$ and $R^B$ are —$CH_2CH(OH)CH_2$—, $R^{10}$, $R^{11}$, $R^{13}$ and $R^{14}$ are independently a monovalent hydrocarbon group of 1 or 2 carbon atoms, $R^{12}$ and $R^{13}$ are independently a linear or branched monovalent hydrocarbon group of from 1 to 6 carbon atoms such as any of those aforementioned and optionally substituted with one or more hydroxyl groups, and $X^{\ominus}$ is $^{\ominus}OC(=O)$— containing group of from 2 to 22 carbon atoms, more specifically from 2 to 12 carbon atoms and still more specifically from 2 to 6 carbon atoms; and, subscript a is 1 to 15 and subscripts h and c each independently is 0 or 1 to 14 subject to the condition that a+b+c≤15, and subscript d is 0 or 1.

$X^{\ominus}$ may therefore be represented by the general formula:

$$^{\ominus}OC(=O)C(R^{16})(R^{17})(R^{18})$$

wherein:

$R^{16}$ and $R^{17}$ are independently hydrogen, hydroxyl or a monovalent hydrocarbon group of from 1 to 3 carbon atoms or hydroxymethyl, and $R^{18}$ is hydrogen, hydroxyl, a monovalent hydrocarbon group of 1 to 20, and specifically 1 to 10, carbon atoms, or a hydroxymethyl group.

Examples of $X^{\ominus}$ include, but are not limited to, those derived from monocarboxylic acids such as acetic acid, propionic acid and butyric acid; dicarboxylic acids such as succinic acid, maleic acid, oxalic acid and tricarboxylic acids; alpha-hydroxy acids such as glycolic acid, lactic acid, citric acid and mandelic acid; beta-hydroxy acids such as hydroxy propionic acids, salicylic acid, carnitine β-hydroxy β-methylbutyric acid and 3-hydroxybutyric acid, dihydroxy acids such as dimethylol propionic acid; and, saturated and unsaturated fatty acids such as caprylic acid, capric acid, caproic acid, oleic acid, myristoleic acid, stearic acid, linoleic acid and erucic acid.

In a one embodiment of silicone surfactant (I), $R^1$ is n-hexyl, $R^2$ and $R^3$ are methyl $R^8$ is 3, $R^9$ is hydrogen or methyl, subscript a is 6 to 9, substrate b is 0 to 2.5, subscript c is 0 and subscript d is 1.

In another embodiment of organosilicon surfactant (I), $R^1$ is $R^4$—$Si(R^5)(R^6)$—$R^7$— in which $R^2$, $R^3$, $R^4$, $R^5$ and $R^6$ are methyl, $R^7$ is a divalent hydrocarbon group of 2 carbon atoms, $R^8$ is propyl or isopropyl, $R^9$ is hydrogen or methyl; subscript a is 6 to 9, subscript b is 0 to 2.5, subscript c is 0 and subscript d is 1.

In yet another preferred embodiment of organosilicon surfactant (I), $R^1$ is $R^4$—$Si(R^5)(R^6)$—$R^7$— in which $R^2$, $R^3$, $R^4$, $R^5$ and $R^6$ are methyl, $R^7$ is a divalent hydrocarbon group of 2 carbon atoms; $R^8$ is propyl or isopropyl, $R^9$ is —$R^A$—$N(R^{10})(R^{11})R^{12}$ in which $R^A$ is —$CH_2CH(OH)CH_2$—, $R^{10}$ and $R^{11}$ are methyl, $R^{12}$ is a linear or branched hydrocarbon of from 3 to 6 carbon atoms and subscript d is 0.

In still another embodiment of organosilicon surfactant (I), $R_1$ is $R_4$—$Si(R_5)(R_6)$—$R_7$— in which $R^2$, $R^3$, $R^4$, $R^5$ and $R^6$ are methyl, $R^7$ is a divalent hydrocarbon group of 2 carbons, $R^8$ is propyl or isopropyl, $R^9$ is —$R^B$—$N^{\oplus}(R^{13})(R^{14})R^{15}X^{\ominus}$ wherein $R^B$ is —$CH_2CH(OH)CH_2$—, $R^{13}$ and $R^{14}$ are methyl, $R^{15}$ is a linear or branched hydrocarbon group of from 3 to 6 carbon atoms with at least one of the carbon atoms being substituted with a hydroxyl group, and $X^{\ominus}$ is derived from dimethylol propionic acid, lactic acid, propionic acid or glycolic acid.

Organosilicon surfactants (I) and methods of their preparation are disclosed in, among others, U.S. Pat. Nos. 7,507,775; 7,645,720; 7,652,072; 7,700,797; 7,879,916; and 7,935,842; and, pending U.S. patent application Ser. No. 62/062,281, filed Oct. 10, 2014, the entire contents of which are incorporated by references herein. Commercially available organosilicon surfactants (I) include Silwet HS-312 spreader, Silwet HS-604 spreader, Silwet HS-508 penetrant, and Silwet HS-429 penetrant, all from Momentive Performance Materials Inc.

Organosilicon surfactants (I) function as penetrants, i.e., as facilitating the penetration within a plant's internal structures of bioactive substances contained in agricultural sprays formulated with the antidrift composition herein, and in many such formulations additionally function to increase the amounts of spray deposited upon plant tissue surfaces and/or the amount of spray that has deposited upon the plant tissues surfaces, such resulting in an increase in plant uptake of the bioactive(s) and consequent increase in its/their effectiveness.

The amount of organosilicon surfactant(s) (I) present in the antidrift composition can vary widely provided it is an amount effective to enhance penetration of bioactive into a plant's internal structure and, advantageously, to increase deposition and/or retention of bioactive-containing spray droplets onto plant surfaces. Thus, e.g., an antidrift composition herein can contain from 1 to 99, more specifically from 1 to 50 and still more specifically from 1 to 10, weight percent of organosilicon surfactant(s) (I) by total, weight of lecithin and organosilicon surfactants (I).

C. Optional Components

The adjuvant composition of the invention can contain one or more optional components such as those known for incorporation in agrochemical formulations, e.g., one or more acidification agents, wetting agents, foam control agents, solvents, water, and the like.

1. Acidification Agent

An acidification agent may be included in the adjuvant composition when the pH of the spray solution is >pH 5. Reducing the pH to between pH 4 and 5 can aid with herbicide uptake and address water hardness issues.

Suitable acidification agents include the carboxylic acids, including the hydroxyl acids, and phosphoric acid, specific non-limiting examples of which include propionic acid, dimethylolpropionic acid, acetic acid, lactic acid, citric acid, ascorbic acid, butyric acid, glycolic acid, valeric acid, cyclopentane carboxylic acid, 2-methyl pentanoic acid, and the like. Where utilized, acidification agent(s) can be present in amounts of up to 50, more specifically up to 30 and still more specifically up to 20 weight percent of the antidrift composition.

2. Wetting Agent

A wetting agent selected from amongst the nonionic, anionic, cationic and zwitterionic surfactants can be incorporated in the antidrift composition herein when it is desired to further reduce the dynamic surface tension of the spray solution, as a means of improving spray droplet deposition.

Non-limiting examples of suitable nonionic surfactant wetting agents include alcohol ethoxylates, alkylpolyglycosides, alkyleneoxide copolymers (random or blocked) of ethyleneoxide with propyleneoxide, butyleneoxide, alkylpolyglycerols, acetylenic diol alkoxylates, and the like. Non-limiting examples of suitable anionic surfactants wetting agents include alkylsulfates (e.g., sodium lauryl sulfate, sodium laurylethoxy sulfates and 2-ethylhexylsulfate), alkylbenzene sulfonates (e.g., sodium dodecylbenxene sulfonates). $C_8$-$C_{18}$ phosphate, mono-, di- and tri-esters with alkyleneoxide, alkyl sarcosinates such as sodium lauryl sarcosinate, and the like. Non-limiting examples of suitable cationic surfactants wetting agents include $C_8$-$C_{18}$ alkoxylated fatty amines and imidazolines. Non-limiting examples of suitable zwiterionic surfactants wetting agents include $C_8$-$C_{18}$ amidopropyl betaines, such as, but not limited to, lauryl betaine, myristyl betaine, lauramidopropyl betaine, soyamidopropyl betaine, laurylamido betaine, oleyl betaine, and the like.

These and other wetting agents may be included in the adjuvant composition in widely varying levels, e.g., up to 80, more specifically up to 40, and still more specifically up to 5, weight percent of such composition.

3. Foam Control Agent

A foam control agent may be included in the adjuvant composition of the invention to suppress the formation of foam. Suitable foam control agents include, without limitation, silica-filled polydimethylsiloxanes or reaction products of silica and a polydimethyl-siloxane.

The amounts of foam control agent present in the adjuvant composition of the invention can vary over a wide range, e.g., from 0.001 to 0.25, and more particularly from 0.005 to 0.1, weight percent thereof.

4. Solvent

One or more solvents may be incorporated in the adjuvant composition of the invention as compatibilization agents.

Suitable optional solvents include, without limitation, the C1-C10 alcohols, the methyl-, ethyl- or isopropyl-fatty acid esters such as methyl oleate, methyl soyate, isopropyl myristate, and the like.

Amounts of such optional solvents where utilized may vary widely, e.g., up to 80, more specifically up to 50 and still more specifically up to 10, weight percent of such composition.

5. Water

Water in widely varying amounts may be incorporated in the adjuvant composition herein in order to compatibilize the formulation. For example, where utilized, water may be present at a level of up to 30, and more specifically of up to 20, weight percent of the adjuvant composition.

6. Preparation of the Adjuvant Composition

Adjuvant compositions in accordance with the invention may be prepared employing procedures well known in the art including without limitation, mechanically blending the lecithin, organosilicon surfactant (I) and optional components, if any, at temperatures ranging from ambient (~15° C.) up to 70° C. The adjuvant compositions may be prepared in a variety of forms such as liquid solutions, dispersions of solids in liquids, dispersion of liquids in liquids, solid mixtures, solid solutions, and the like.

D. Agrochemical Formulations Formulated With the Adjuvant Composition

The adjuvant composition herein will typically be combined with any of a variety of agrochemicals including, without limitation, pesticides, fertilizers and micronutrients, and the like, in accordance with procedures well known in the art and in amounts sufficient to improve, increase or enhance the delivery, availability and/or efficacy of their bioactive component(s).

For example, agrochemical formulations, may be prepared by combining an adjuvant composition of the invention either as a tank-mix, or as an "in-can" formulation. The term "tank-mix" means the addition of at least one agrochemical to a spray medium, such as water or oil, at the point of use. The term "in-can" refers to a formulation or -concentrate containing at least one agrochemical component. The "in-can" formulation may then be diluted to use concentration at the point of use, typically in a tank-mix, or it may be used undiluted.

The term "pesticide" herein means any compound used to destroy pests, e.g., rodenticides, insecticides, miticides, fungicides, herbicides, and the like. Typical uses for pesticides include agricultural, horticultural, turf, ornamental, home and garden, veterinary and forestry applications. The pesticidal formulations of the present invention also include al least one pesticide, where the quaternary organosilicon surfactant of the present invention is present in an amount sufficient to deliver between 0.005% and 2% to the final use concentration, either as a concentrate or diluted in a tank mix. Optionally, the pesticidal formulation may include excipients, cosurfactants, solvents, foam control agents, deposition aids, drift retardants, biologicals, micronutrients, fertilizers, and the like. Illustrative examples of pesticides that can be employed include, but are not limited to mitotic disrupters, lipid biosynthesis inhibitors, cell wall inhibitors, and cell membrane disrupters. The amount of pesticide employed in agrochemical formulations may vary with the type of pesticide employed. More specific examples of pesticide compounds that can be used with the formulations include, but are not limited to, herbicides and growth regulators such as phenoxy acetic acids, phenoxy propionic acids, phenoxy butyric acids, benzoic acids, triazines and s-triazines, substituted ureas, uracils, bentazon, desmedipham, methazole, phenmedipham, pyridate, amitrole, clomazone, fluridone, norflurazone, dinitroanilines, isopropalin, oryzalin, pendimethalin, prodiamine, trifluralin, glyphosate, sulfonylureas, imidazolinones, dethodim, diclofop-methyl, fenoxaprop-ethyl, fluazifop-p-butyl, haloxyfop-methyl, quizalofop, sethoxydim, dichlobenil, isoxaben, and bipyridylium compounds.

Fungicide compositions that can be used with the present invention include, but are not limited to, aldimorph, tridemorph, dodemorph, dimethomorph; flusilazol, azaconazole, cyproconazole, epoxiconazole, furconazole, propiconazole, tebuconazole and the like; imazalil, thiophanate, benomyl carbendazim, chlorothialonil; dieloran, trifloxystrobin, fluoxystrobin, dimoxystrobin, azoxystrobin, furcaranil, prochloraz, flusulfamide, famoxadone, captan, maneb, mancozeb, dodicin, dodine, and metalaxyl.

Insecticides, including larvacide, miticide and ovacide compounds that can be used with the composition of the present invention include, but are not limited to, Bacillus thuringiensis, spinosad, abamectin, doramectin, lepimectin, pyrethrins, carbaryl, primicarb, aldicarb, methomyl, amitraz, boric acid, chlordimeform, novaluron, bistrifluron, triflumuron, diflubenzuron, imidacloprid, diazinon, acephate, endosulfan, kelevan, dimethoate, azinphos-ethyl, azinphosmethyl, izoxathion, chlorpyrifos, clofentezine, lambda-cyhalothrin, permethrin, bifenthrin, cypermethrin, and the like.

Fertilizers, and micronutrients include, but are not limited to, zinc sulfate, ferrous sulfate, ammonium sulfate, urea, urea ammonium nitrogen, ammonium thiosulfate, potassium sulfate, monoammonium phosphate, urea phosphate, calcium nitrate, boric acid, potassium and sodium salts of boric acid, phosphoric acid, magnesium hydroxide, manganese carbonate, calcium polysulfide, copper sulfate, manganese sulfate, iron sulfate, calcium sulfate, sodium molybdate and calcium chloride.

The pesticide or fertilizer may be a liquid or a solid. If a solid, it is preferable that it is soluble in a solvent, or the quaternary organosilicon surfactant of the present invention, prior to application, and the silicone may act as a solvent, or surfactant for such solubility or additional surfactants may perform this function.

Agricultural excipients such as buffers, preservatives and other standard excipients known in the art also may be included in the agrochemical composition in known and conventional amounts.

Solvents may also be included in the agrochemical formulations. Examples include water, alcohols, aromatic solvents, oils (i.e. mineral oil, vegetable oil, silicone oil, and so forth), lower alkyl esters of vegetable oils, fatty acids, ketones, glycols, polyethylene glycols, diols, paraffinics, and so forth. Particular solvents include, without limitation, 2,2,4-trimethyl, 1,3-pentane diol and alkoxylated (especially ethoxylated) versions thereof as disclosed in U.S. Pat. No. 5,674,832, the contents of which are incorporated by reference herein, and N-methyl-2-pyrrolidone.

Wetting agents and cosurfactants suitable for agrochemical formulations include nonionie, cationic, anionic, amphoteric, zwitterionic, polymeric surfactants, or any mixture thereof. Surfactants are typically hydrocarbon based, silicone based or fluorocarbon based. Cosurfactants, that have short chain hydrophobes that do not interfere with superspreading as described in U.S. Pat. No. 5,558,806, incorporated by reference herein, are also useful.

Useful surfactants include, without limitation, alkoxylates-, especially ethoxylate-containing block copolymers including copolymers of ethylene oxide, propylene oxide, butylene oxide, and mixtures thereof; alkylarylalkoxylates, especially ethoxylates or propoxylates and their derivatives including alkyl phenol ethoxylate; arylarylalkoxylates, especially ethoxylates or propoxylates, and their derivatives; amine alkoxylates, especially amine ethoxylates; fatty acid alkoxylates; fatty alcohol alkoxylates; alkyl sulfonates; alkyl benzene and alkyl naphthalene sulfonates; sulfated fatty alcohols, amines or acid amides; acid esters of sodium isethionate; esters of sodium sulfosuccinate; sulfated or sulfonated fatty acid esters; petroleum sulfonates; N-acyl sarcosinates; alkyl polyglycosides; alkyl ethoxylated amines; and so forth. Specific examples of useful surfactants include, among others, alkyl acetylenic diols (Surfynol or Dynol from Air Products), 2-ethyl hexyl sulfate, isodecyl alcohol ethoxylates (e.g., Rhodasurf DA 530 from Rhodia/Solvay, ethylene diamine alkoxylates (Tetronics from BASF), ethylene oxide/propylene oxide copolymer (Pluronics from BASF), Gemini type surfactants (Rhodia/Solvay) and diphenyl ether Gemini type surfactants (e.g., Dowfax from Dow Chemical). Preferred surfactants include ethylene oxide/propylene oxide copolymers (EO/PO); amine ethoxylates; alkyl polyglycosides; oxo-tridecyl alcohol ethoxylates, and so forth.

In a preferred embodiment, the agrochemical formulation of the present invention further comprises one or more herbicides, insecticides, growth regulators, fungicides, miticides, acaricides, fertilizers, biologicals, plant nutritionals, micronutrients, biocides, paraffinic mineral oil, methylated seed oils (i.e. methylsoyate or methylcanolate), vegetable oils (such as soybean oil and canola oil), water conditioning agents such as Choice® (Loveland Industries, Greeley, Colo.) and Quest® (Helena Chemical, Collierville, Tenn.), modified clays such as Surround® (BASF), foam control agents, surfactants, wetting agents, dispersants, emulsifiers, deposition, aids, anti-drift components, and water.

The lecithin components of the adjuvant compositions illustrated in the examples are listed below in Table 1:

TABLE 1

Lecithin Components

| Lecithin | Designation in the Examples | Description | Source | Form | Acetone Insolubles | HLB |
|---|---|---|---|---|---|---|
| Alcolec F-100 | Lecithin-1 | Soy Lecithins | American Lecithin Co. | Powder | 97% | 7 |
| Alcolec SGU | Lecithin-2 | Soy Lecithins | American Lecithin Co. | Fluid | 62% | 4 |
| Alcolec 40P | Lecithin-3 | Soy Lecithins | American Lecithin Co. | Powder | 97% | 8 |
| Yelkin TS | Lecithin-4 | Soy Lecithins | Archer Daniels Midland Co. | Liquid | 62% | 4 |
| Ultralec P | Lecithin-5 | Soy Lecithins | Archer Daniels Midland Co. | Powder | 97% | 7 |

The organosilicon surfactant (I) components of the adjuvant composition illustrated in the examples are listed below in Table 2:

TABLE 2

Organosilicon Surfactants

| Surfactant | $R^1$ | $R^2$ | $R^3$ | Z |
|---|---|---|---|---|
| OSIL-1 | $(CH_3)_3SiCH_2CH_2-$ | $CH_3$ | $CH_3$ | $-CH_2CH_2-CH_2O(CH_2CH_2O)_8-CH_3$ |
| OSIL-2 | $(CH_3)_3SiCH_2CH_2-$ | $CH_3$ | $CH_3$ | See Z below |

Z = $-CH_2CH_2-CH_2OCH_2CH(OH)CH_2-N^{\oplus}(CH_3)(CH_3)-CH_2CH_2CH-OH^{\ominus}O-C(=O)-C(CH_2OH)(CH_2OH)CH_3$ The wetting agents included in the adjuvant compositions illustrated in the examples are listed in Table 3.

TABLE 3

Wetting Agents

| Wetting Agent | Designation in the Examples | Description | Source | HLB |
|---|---|---|---|---|
| Lutensol XL-50 | NIS-1 | Alcohol Alkoxylate | BASF | 9.0 |
| Tergitol 15-S-3 | NIS-2 | Alcohol Ethoxylate | Dow Chemical | 8.0 |
| Tergitol 15-S-5 | NIS-3 | Alcohol Ethoxylate | Dow Chemical | 10.5 |
| Tergitol 15-S-7 | NIS-4 | Alcohol Ethoxylate | Dow Chemical | 12.1 |
| Tergitol 15-S-9 | NIS-5 | Alcohol Ethoxylate | Dow Chemical | 13.3 |
| Tergitol TMN-6 | NIS-6 | Alcohol Ethoxylate | Dow Chemical | 11.7 |
| Rhodasurf DA-530 | NIS-7 | Alcohol Ethoxylate | Solvay | 10.5 |
| Genapol X-080 | NIS-8 | Alcohol Ethoxylate | Clariant | 13.0 |

The lecithin-based antidrift adjuvant composition LI-700 (Loveland Products, Inc.) was used in the examples as a benchmark for comparison with adjuvant compositions in accordance with the invention. According to its label description LI-700 contains the lecithin compound phosphatidyl-choline, methyl acetic acid and alkyl polyoxyethylene ether, 80% concentration.

The adjuvant compositions of the invention were prepared as physical mixtures of the ingredients by adding the lecithin, water (3% of total) and propionic acid (2.6% of total) to a 250 ml, plastic beaker positioned in a heating bath set between 45-55° C. The components were mixed for 5 minutes at 200 rpm using a Lightnin' Mixer fitted with a Cowles blade. Thereafter, the organosilicon surfactant (I) and non-ionic wetting agent were added and mixed for 3.0 minutes at 250 rpm at which point the remaining water and propionic acid were added and then mixed for an additional 15 minutes at 300 rpm. The heating bath was then removed and the adjuvant composition allowed to cool to ambient temperature (~22° C.). At this point, 0.1% antifoaming agent was added and mixed into the final composition followed by filtration.

Example 1

Employing the foregoing procedure, adjuvant compositions Sil-1 to Sil-15 were prepared with the components and amounts thereof set forth in Table 4 below. SAG 1572 is a foam control agent from Momentive Performance Materials, Inc.

TABLE 4

Adjuvant Compositions Sil-1 to Sil-15

| Components | HLB | Al | PC | MW | Sil-1 | Sil-2 | Sil-3 | Sil-4 | Sil-5 | Sil-6 | Sil-7 |
|---|---|---|---|---|---|---|---|---|---|---|---|
| Lecithin-1 | 4.0 | 60 | 14 | | 30.00 | | 17.50 | 17.50 | 16.00 | 25.00 | 25.00 |
| Lecithin-2 | 7.0 | 97 | 24 | | 5.00 | 35.00 | 17.50 | 17.50 | 16.00 | 10.00 | 10.00 |
| Lecithin-3 | 8.0 | 97 | 40 | | | | | | | | |
| Lecithin-4 | 4.0 | 62 | 14 | | | | | | | | |
| Lecithin-5 | 7.0 | 97 | 24 | | | | | | | | |
| OSIL-1 | 8.5 | | | | 3.65 | 3.65 | 3.40 | 2.00 | 3.65 | 2.50 | 3.65 |
| NIS-1 | 9.0 | | | | 5.35 | 5.35 | 6.00 | 7.00 | 5.35 | 7.50 | |
| NIS-8 | 13.0 | | | | | | | | | | 5.35 |
| NIS-7 | 11.0 | | | | | | | | | | |
| Water | | | | | 20.90 | 20.90 | 20.50 | 25.90 | 23.90 | 19.90 | 20.90 |
| SAG 1572 | | | | | 0.10 | 0.10 | 0.10 | 0.10 | 0.10 | 0.10 | 0.10 |
| Propionic Acid | | | | 74.1 | 35.00 | 35.00 | 35.00 | | | 35.00 | 35.00 |
| Lactic Acid | | | | 90.1 | | | | 30.00 | 35.00 | | |
| Glycolic Acid | | | | 76.1 | | | | | | | |
| Acetic Acid | | | | 60.1 | | | | | | | |
| Citric Acid | | | | 192.2 | | | | | | | |
| Total (%) | | | | | 100.00 | 100.00 | 100.00 | 100.00 | 100.00 | 100.00 | 100.00 |
| HLB Lecithin | | | | | 4.4 | 7.0 | 5.5 | 5.5 | 5.5 | 4.9 | 4.9 |
| HLB Surfactants | | | | | 8.8 | 8.8 | 9.2 | 8.9 | 8.8 | 9.9 | 11.2 |
| % Al | | | | | 65.3 | 97.0 | 78.5 | 78.5 | 71.8 | 70.6 | 70.6 |
| % PC | | | | | 15.4 | 24.0 | 19.0 | 19.0 | 17.4 | 16.9 | 16.9 |
| wt % Surfactant | | | | | 9.0 | 9.0 | 9.4 | 9.0 | 9.0 | 10.0 | 9.0 |
| Acid Eq/100 g | | | | | 0.5 | 0.5 | 0.5 | 0.3 | 0.4 | 0.5 | 0.5 |

| Components | Sil-8 | Sil-9 | Sil-10 | Sil-11 | Sil-12 | Sil-13 | Sil-14 | Sil-15 |
|---|---|---|---|---|---|---|---|---|
| Lecithin-1 | | | 25.00 | 10.00 | 26.25 | 24.00 | 26.00 | 26.25 |
| Lecithin-2 | | | 10.00 | 25.00 | 8.75 | | | 8.75 |
| Lecithin-3 | | | | | | 8.00 | 9.00 | |
| Lecithin-4 | 20.00 | 35.00 | | | | | | |
| Lecithin-5 | 15.00 | | | | | | | |
| OSIL-1 | 3.65 | 3.65 | 3.65 | 3.40 | 3.65 | 3.40 | 3.40 | 1.00 |
| NIS-1 | | 5.35 | 5.35 | 6.00 | 6.35 | 6.60 | 6.00 | |
| NIS-8 | | | | | | | | |
| NIS-7 | 5.35 | | | | | | | 6.00 |
| Water | 20.90 | 20.90 | 20.90 | 20.50 | 19.90 | 27.90 | 20.50 | 27.90 |
| SAG 1572 | 0.10 | 0.10 | 0.10 | 0.10 | 0.10 | 0.10 | 0.10 | 0.10 |
| Propionic Acid | 35.00 | 35.00 | | 35.00 | 35.00 | | | |
| Lactic Acid | | | | | | | | |

TABLE 4-continued

| Adjuvant Compositions Sil-1 to Sil-15 | | | | | | | | |
|---|---|---|---|---|---|---|---|---|
| Glycolic Acid | | | 35.00 | | | | | |
| Acetic Acid | | | | | | 30.00 | 35.00 | |
| Citric Acid | | | | | | | | 30.00 |
| Total (%) | 100.00 | 100.00 | 100.00 | 100.00 | 100.00 | 100.00 | 100.00 | 100.00 |
| HLB Lecithin | 5.3 | 4.0 | 4.9 | 6.1 | 4.8 | 4.6 | 5.0 | 4.8 |
| HLB Surfactants | 10.0 | 8.8 | 8.8 | 9.2 | 9.8 | 9.8 | 9.2 | 8.3 |
| % Al | 77.0 | 62.0 | 70.6 | 86.4 | 69.3 | 63.3 | 69.5 | 69.3 |
| % PC | 18.3 | 14.0 | 16.9 | 21.1 | 16.5 | 18.7 | 20.7 | 16.5 |
| wt % Surfactant | 9.0 | 9.0 | 9.0 | 9.4 | 10.0 | 10.0 | 9.4 | 7.0 |
| Acid Eq/100 g | 0.5 | 0.5 | 0.5 | 0.5 | 0.5 | 0.5 | 0.6 | 0.2 |

Table 5 sets forth the components and the amounts thereof (wt. %) of three adjuvant compositions in accordance with the invention (PI, P-II and P-III). The dynamic surface tension (DST) properties of adjuvant compositions P-I and LI-700 were measured using a Kruss BP-1 maximum bubble pressure tensiometer. As the data in FIG. 1 show, P-I exhibited lower DSTs at 0.5% and 0.25% levels than that of LI-700 at 0.5% level.

TABLE 5

| Adjuvant Compositions | | | |
|---|---|---|---|
| Components | P-I | P-II | P-III |
| Lecithin-1 | 35.00 | 35.00 | 35.00 |
| Propionic Acid | 35.00 | 35.00 | 35.00 |
| OSIL-1 | 3.65 | 5.48 | 7.30 |
| NIS-1 | 5.35 | 8.02 | 10.70 |
| SAG 1572 | 0.10 | 0.10 | 0.10 |
| Water | 20.90 | 16.40 | 11.90 |
| Total | 100.00 | 100.00 | 100.00 |

Example 2

Adjuvant compositions in accordance with the invention (Sil-16 to Sil-19) were prepared using a fixed ratio of lecithin and a fixed ratio of organosilicon surfactant (I) while varying the wetting agent type. Table 6 below sets forth the components of the compositions and their amounts.

TABLE 6

| Adjuvant Compositions Sil-16 to Sil-19 | | | | | |
|---|---|---|---|---|---|
| Components | HLB | Sil-16 | Sil-17 | Sil-18 | Sil-19 |
| Lecithin-1 | 7.0 | 35.00 | 35.00 | 35.00 | 35.00 |
| OSIL-1 | 8.5 | 3.65 | 3.65 | 3.65 | 3.65 |
| NIS-1 | 9.0 | | | | |
| NIS-2 | 8.0 | 5.35 | | | |
| NIS-3 | 10.5 | | 5.35 | | |
| NIS-4 | 12.1 | | | 5.35 | |
| NIS-5 | 13.3 | | | | 5.35 |
| Water | | 20.90 | 20.90 | 20.90 | 20.90 |
| SAG 1572 | | 0.10 | 0.10 | 0.10 | 0.10 |
| Propionic Acid | | 35.00 | 35.00 | 35.00 | 35.00 |
| Total (%) | | 100.00 | 100.00 | 100.00 | 100.00 |
| HLB Lecithin | | 7.0 | 7.0 | 7.0 | 7.0 |
| HLB Surfactants | | 8.2 | 9.7 | 10.6 | 11.4 |

The data in Table 7 below shows that the adjuvant compositions herein form stable formulations when secondary alcohol ethoxylates are used as the wetting agent, similar to the results obtained with primary alcohol ethoxylate wetting agents.

TABLE 7

| Stability of Adjuvant Compositions of Table 6 | | | | |
|---|---|---|---|---|
| Stability | Sil-16 | Sil-17 | Sil-18 | Sil-19 |
| Initial | Stable/Hazy | Stable/Hazy | Stable/Hazy | Stable/Clear |
| After 24 hr | Stable/Clear/Light sediment | Stable/Clear/Light sediment | Stable/Clear/Light sediment | Stable/Clear/Light sediment |
| After 5 days | Stable/Clear/Light sediment | Stable/Clear/Light sediment | Stable/Clear/Light sediment | Stable/Clear/Light sediment |

Example 4

Many types of pesticides are weak acids and show greater efficacy due to improved penetration into plant structures under acidic conditions. The data in Table 8 below show the ability of an adjuvant composition of the invention (Sil-6) to reduce the pH of deionized (DI) water, hard water containing 300 ppm of $Ca^{2o}$ and $Mg^{2+}$ and spray solutions of glyphosate-IPA and 2,4-D amine in hard water. The pH conditioning ability was equivalent to that of comparative antidrift composition LI-700.

TABLE 8

| Effect of Adjuvant Composition on Water Conditioning | | | |
|---|---|---|---|
| | | pH | |
| Antidrift Composition | As is | w/ 0.5 wt % Sil-6 | w/ 0.5 wt % LI-700 |
| DI water | 7.3 | 3.4 | 3.4 |
| 300 ppm hard water | 5.6 | 3.4 | 3.3 |
| 2.0% Gly-IPA in DI water | 4.5 | 4.1 | 4.1 |
| 1.0 wt % 2,4-D DMA in DI water | 5.2 | 4.0 | 4.0 |
| 2.0% Gly-IPA in 300 ppm hard water | 4.5 | 4.1 | 4.1 |
| 1.0 wt % 2,4-D DMA in 300 ppm hard water | 5.2 | 4.0 | 4.0 |

Example 5

The dispersibility and emulsion stability in soft and hard water was evaluated by addition of 1 mL of the adjuvant composition Sil-3 or comparative antidrift adjuvant LI-700 to 99 mL of water in a graduated cylinder. The cylinder was then manually inverted ten times. The emulsion stability was observed at 1 hour for appearance and for the amount of separation recorded as mL of cream, foam or oil. Additionally, the number of inversions required to completely disperse each composition was determined: 1-3=disperses readily; 4-6=disperses slowly; 7-10=disperses with difficulty. As the data in Table 9 show, the water hardness ranged from 100 to 1000 ppm of $Ca^{2+}$ and $Mg^{2+}$.

The data in Table 9 below show that adjuvant composition Sil-3 disperses more readily and provides improved emulsion stability in both soft and hard, water compared to that of comparative antidrift adjuvant composition LI-700.

TABLE 9

Emulsion Stability in Soft and Hard Water

| Adjuvant Composition | Blooming | Phase sep. (1 hr) | No. of Inversions | Foam (mL) | Cream (mL) |
|---|---|---|---|---|---|
| 100 ppm soft water ||||||
| Sil-3 | Yes | No | 3-4 | 0.0 | 0.0 |
| LI 700 | No | Oil ring | 3 | 0.0 | ~0.1 mL oil |
| 300 ppm hard water ||||||
| Sil-3 | Yes | No | 2-3 | 0.0 | 0.0 |
| LI 700 | No | Oil ring | 3 | 0.0 | ~0.2 mL oil |
| 1000 ppm hard water ||||||
| Sil-3 | Yes | No | 2 | 0.0 | 0.0 |
| LI 700 | No | Oil ring | 3 | 0.0 | ~0.4 mL oil |

Example 6

Freeze-thaw stability of adjuvant compositions was evaluated, through 5 cycles of leaving each tested composition overnight at −5° C. and evaluating its appearance after 2 hours at room temperature. After each cycle, adjuvant composition Sil-3 formed a homogenous dispersion after thawing in contrast to comparative adjuvant composition L-700 which developed an upper layer of insoluble material that could only be redispersed vigorous shaking.

Example 7

Uptake of $^{14}C$-glyphosate herbicide into barnyardgrass (*Echinochloa crus-galli*) was measured at 2 and 24 hours after treatment according to the method described by Gaskin et al. (Gaskin, R. E.; Stevens, P. J. G. Pestic. Sci. 38: 185-192, 1992) thereby establishing the impact of the surfactant component of the adjuvant on the speed of uptake. Uptake was determined on the adaxial surface of the youngest fully expanded leaf; plant at 4 leaf stage, about 10 cm tall. The glyphosate solution (Gly-IPA) was applied at a dilution rate equivalent to 750 g Gly-IPA/100 L water. The data in Table 10 below demonstrates that adjuvant compositions Sil-6 and Sil-10 provided faster uptake at 2 hours after treatment than comparative adjuvant LI-700.

TABLE 10

Uptake of Gly-IPA into Barnyardgrass After 2 hours

| Adjuvant Composition | Conc. % w/v | Uptake % 2 HAT |
|---|---|---|
| None | — | 1.2 g |
| LI-700 | 0.50 | 31.0 f |
| Sil-6 | 0.125 | 30.4 f |
| Sil-6 | 0.25 | 40.6 e |
| Sil-6 | 0.50 | 30.3 f |
| Sil-10 | 0.125 | 37.5 e |
| Sil-10 | 0.25 | 36.6 e |
| Sil-10 | 0.50 | 27.8 f |

Means sharing common postscripts are NSD (LSD test, P = 0.05). Growing conditions were 23° C. day/15° C. night, 14 h photoperiod, 70% RH, ~500 µmol/m$^2$/sec. Plants were approx 4 weeks old, 4-5 leaves, 10 cm tall.

Example 8

Spray droplet adhesion as a percent of impacted droplets was determined as previously described (Stevens et al. Pestic. Sci. 38: 237-245, 1993) employing a piezoelectric droplet generator with a 200 µm nozzle orifice forming mono-sized droplets of about 400 µm. The droplet freefall distance was 53 cm with a velocity of approximately 1 m/s. Cabbage foliage (difficult-to-wet) was used as the impaction surface with a leaf angle of 22.5°. The data in Table 11 below show that adjuvant compositions Sil-6 and Sil-10 provided similar or better droplet adhesion on cabbage leaf relative to comparative antidrift adjuvant LI-700. Adhesion increased with an increase in adjuvant concentration.

TABLE 11

Effect of Antidrift Composition on Droplet Adhesion

| Antidrift Composition | Conc. % w/v | Adhesion % |
|---|---|---|
| Sil-6 | 0.125 | 40 d |
| Sil-6 | 0.25 | 46 cd |
| Sil-6 | 0.50 | 69 a |
| Sil-10 | 0.125 | 41 d |
| Sil-10 | 0.25 | 53 bc |
| Sil-10 | 0.50 | 67 a |
| LI-700 | 0.50 | 61 ab |

Means sharing common postscripts are not significantly different ($P_{0.05}$, LSD test).

Example 9

The uptake of $^{14}C$-2,4-dichlorophenoxyacetic acid, dimethylamine salt (2,4-D DMA salt) (1% a.e./100 L/ha) was determined for the eanola plant at 2 and 24 hours after treatment according to the method described by Lui, in Pro. 18th Asian-Pacific Weed Sci. Soc. Conf., pp. 561-566, 2001.

The data in Table 12 below demonstrate that adjuvant compositions Sil-3 and Sil-11 showed improved uptake of 2,4-D DMA by canola leaf relative to the comparative antidrift adjuvant LI-700. Even at half the concentration, a significant improvement in uptake was observed.

TABLE 12

Uptake of 2,4-D DMA by Canola Leaf After 24 Hours

| Adjuvant Treatment | Conc. % w/v | Uptake % 24 HAT |
|---|---|---|
| Sil-3 | 0.25 | 69.1 ab |
| Sil-3 | 0.5 | 66.8 abc |
| Sil-11 | 0.25 | 59.6 c |
| Sil-11 | 0.5 | 61.0 c |
| LI-700 | 0.25 | 59.6 c |
| LI-700 | 0.5 | 64.5 bc |

Means sharing common postscripts are NSD (LSD test, P = 0.05). Growing conditions were 20/15° C., 12 h photoperiod, 70% RH, ~500 µmol/m$^2$/sec. Plants were approx 4 weeks old, 4-5 leaf stage, 10 cm tall.

Example 10

The droplet adhesion of aqueous spray solutions containing 2,4-D and adjuvant composition was evaluated on difficult-to-wet barnyardgrass leaves (the contact angle of a 20 wt % aqueous acetone solution on the adaxial surface of the leaf is 180°). Droplets with a diameter of approximately 400 μm were impacted from a height of 53 cm upon leaves oriented at a 22.5° slope.

All test treatments contained 2,4-D DMA salt analytical grade (Nufarm) at 1% and fluorescent dye (Uvitex NFW 450, Huntsman) at 1%. The adjuvant compositions were added at 0.25% or 0.50%. The test data are set forth in Table 13 below. As these data show, antidrift adjuvant composition Sil-3 gave better droplet adhesion with 2,4-D DMA in both concentrations relative to comparative antidrift adjuvant composition LI-700. Such result, in combination with the superior uptake shown in Table 10, translates into higher total available doses (uptake×adhesion).

TABLE 13

Effect of Adjuvant Composition on Droplet Adhesion on Barnyardgrass

| Adjuvant Composition | Conc. % w/v | Adhesion % |
|---|---|---|
| Sil-3 | 0.25 | 21 b |
| Sil-3 | 0.50 | 32 a |
| LI-700 | 0.25 | 18 b |
| LI-700 | 0.50 | 37 a |

Means sharing common postscripts are not significantly different (P0.05, LSD test)

Example 11

Adjuvant compositions Sil-2, Sil-3 and LI-700 were also evaluated for antidrift performance. The antidrift effect was tested with glyphosate-IPA solutions (Rodeo, Dow AgroSciences) at 1.0% a.e./L. alone and with 0.25% or 0.50% antidrift adjuvant. The methodology was as follows: one nozzle and seven spray solutions were analyzed with a Sympatec Helos Vario KR particle size analyzer as described in Henry et al., W.E 2014. In: Carmine S. ed. Pesticide Formulation and Delivery Systems: 33rd Volume, "Sustainability: Contributions from Formulation Technology", 23-25 Oct. 2012. Atlanta, USA, pp. 129-138. The relationship of venturi nozzles and adjuvant selection on spray quality is described in Castelani P. ed., Proceedings of the 10th International Symposium on Adjuvants for Agrochemicals, 22-26 Apr. 2013, Foz Do Iguaçu, Brazil. pp. 269-272. With the R7 lens installed, the analyzer is capable of detecting particle sizes within a range of from 18 to 3,500 microns using laser diffraction to determine particle size distribution. The width of the nozzle plume was analyzed by moving the nozzle across the laser by means of a linear actuator. All testing was performed in a low speed wind tunnel at 15 mph. Seven spray solutions were evaluated through one nozzle, with each treatment being replicated at least three times. The XR11008 nozzle was tested at 40 psi.

Dv10 is the micron size (μm) at which 10 percent of the spray volume is of the reported size or smaller. Dv50 and Dv90 are of similar significance. The percent less than 10.5 μm (Pet<105 μm) is the percentage of spray volume that is 105 μm and smaller with the percents less than 141 μm (Pet<141 μm), 150 μm (Pet<150 μm), 210 μm (Pet<210 μm), and 730 μm (Pet<730 μm) being similar measurements. The data were analyzed using a mixed model ANOVA (PROC MIXED) with replication set as random in the software SAS version 9.2. The mean separation was conducted at the $\alpha$=0.05 level using a Tukey adjustment.

The data in FIG. 3 show that antidrift compositions Sil-2 and Sil-3 delivered equivalent to better drift control compared with that of the comparative antidrift composition L-700.

Example 12

Trisiloxane alkoxylates (TSAs) are highly surface active and as a result can produce a very stable foam. Conventional antifoam compounds based on polydimethylsiloxane (PDMs) oils have proven to be ineffective in controlling foam generated by TSA surfactants (Policello et. al., Pesticide Formulations and Application Systems: 17th. Volume, ASTM STP 1328, G. Robert Goss, Michael J. Hopkinson, and Herbert M. Collins, Eds., American Society for Testing and Materials, 1997).

The foam profile was tested with samples containing 0.5% of the antidrift adjuvants using a sparge test, in this method, 200 mL of the antidrift adjuvant solution is added to a 1000 mL graduate cylinder. A metal tube having a porous metallic membrane in the bottom is connected to a gas flow controller and inserted in the solution. Nitrogen is sparged in the solution at 1.0 L/min. for 1 min. and the foam level is recorded at initial, 1, 2, 5 and 10 minutes. The data in FIG. 4 show that antidrift composition Sil-7 of the invention, which contains 0.1% foam control agent, delivered significantly foam control that that of antidrift composition LI-700.

Example 13

Antidrift adjuvant compositions based on trisiloxane alkoxylates are hydrolytically unstable and undergo decomposition when the pH is below 6.5. The rate of decomposition increases as the pH decreases below this level. The pH of the antidrift compositions of the invention are typically <pH 3.5. Therefore, the use of a trisiloxane alkoxylate leads to rapid hydrolysis which is observed as an increase in DST. This acid instability of trisiloxane alkoxylates makes them unsuitable for use in antidrift adjuvant compositions.

Two antidrift adjuvant compositions were prepared to demonstrate the difference in hydrolytic stability between a conventional trisiloxane alkoxylate, specifically, Silwet L-77, which has the structure $(CH_3)_3SiOSi(CH_3)(Z)\ OSi(CH_3)_3$ in which Z is $-CH_3CH_2-CH_2O(CH_2CH_2O)_8-CH_3$ (used in antidrift composition Sil-20) and the organosilicon surfactant OSil (see Table 1) (used in antidrift composition Sil-21). The stability data are set forth in Table 14 below.

TABLE 14

Hydrolylic Stability of Antidrift Compositions Sil-20 and Sil-21

| Components | Sil-20 | Sil-21 |
|---|---|---|
| Alcolec F-100 | 17.50 | 35.00 |
| Alcolec SGU | 17.50 | 0.00 |
| Silwet L-77 | 5.00 | 0.00 |
| Water | 25.00 | 16.4 |
| OSIL-1 | 0.00 | 5.48 |
| NIS-1 | 0.00 | 8.02 |
| SAG 1572 | 0.00 | 0.10 |
| Propionic Acid | 35.00 | 35.00 |
| Total (%) | 100.00 | 100.00 |

A 0.5% solution of Sil-20 was prepared in distilled water and its DST measured initially and after 20 hours (FIG. 5). Similarly, to demonstrate the stability of Sil-21 the DST (0.25%) was measured initially and after storage for 7 weeks.

The data in FIG. 5 show the increase in the DST profile of Sil-20 due to hydrolysis of the trisiloxane alkoxylate surfactant after 20 hours. In contrast to this result, the data in FIG. 6 show that Sil-21 remained stable, showing no significant change in DST after 7 weeks of storage.

Example 14

Spray trials were conducted to evaluate the impact of the compositions of the present invention on the field efficacy of Rodeo from Dow AgroSciences (Glyphosate-Isopropylammonium salt at 53.8%). Each spray trial was arranged as a randomized complete block design, with eight treatments and four replications of each treatment. The plot size was 3×7 m. The target weeds were hairy crabgrass (*Digitaria sanguinalis*), smooth crabgrass (*Digitaria ischaemum*) and ribwort plantain (*Plantago lanceolate*). The Rodeo was applied at 0.80 L/ha (0.38 a.e./ha) alone or in combination with adjuvants. The adjuvants, either SIL-3 (Table 4) or LI-700, were applied at 0.125, 0.25 and 0.50 L/ha. The spray volume was 100 L/ha for all treatments. Weed growth stage, number of weeds per m² and the percentage of ground coverage was assessed before application. Weed control after treatment, was assessed using a percentage scale whereby 0=no control and 100=complete control.

Figure 8:
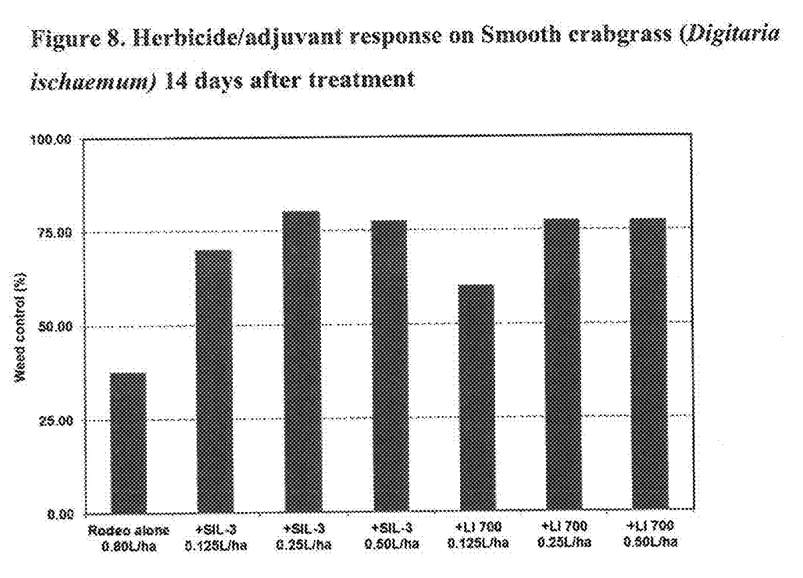
Figure 9:
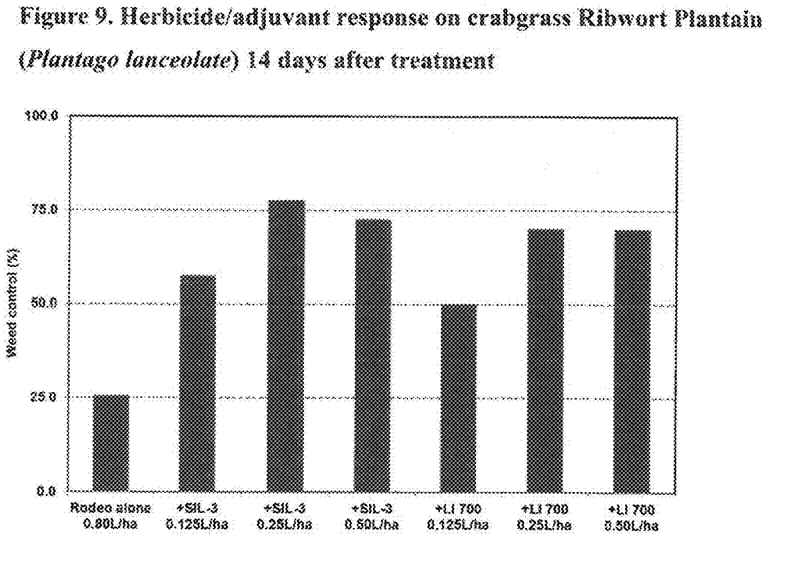

The graphical data in FIGS. 7, 8 and 9 demonstrate that the adjuvant compositions of the present invention delivered better overall weed control than Rodeo alone or Rodeo containing the antidrift adjuvant LI-700.

While the invention has been described with reference to particular embodiments, those skilled in the art will understand that various changes may be made and equivalents may be substituted for elements thereof without departing from the scope of the invention. It is intended that the invention not be limited to the particular embodiments disclosed but that it include all embodiments falling within the scope of the appended claims.

The invention claimed is:

1. An adjuvant composition comprising:
   a) lecithin;
   b) organosilicon surfactant of general formula (I):

$$R^1\text{—}Si(R^2)(R^3)\text{—}Z \quad (I)$$

wherein:
   $R^1$ is a linear or branched monovalent hydrocarbon group of from 1 to 8 carbon atoms or a $R^4$—Si($R^5$)($R^6$)—$R^7$— group in which $R^4$ is a linear or branched monovalent hydrocarbon group of from 1 to 8 carbon atoms, $R^5$ and $R^6$ are independently a linear or branched monovalent hydrocarbon group of from 1 to 4 carbon atoms and $R^7$ is a linear or branched divalent hydrocarbon group of from 1 to 4 carbon atoms; $R^2$ and $R^3$ are independently a linear or branched monovalent hydrocarbon group of from 1 to 4 carbon atoms; and, Z is an alkylene oxide-containing group of up to 15 alkylene oxide units with each unit independently containing from 1 to 4 carbon atoms; a cationic group or a quaternary group free of alkyl halide;
   c) at least one acidification agent; and
   d) at least one wetting agent;
   wherein the lecithin contains from 10 to 70 weight percent phosphatidylcholine with the balance being selected from phosphatidylethanolamine, phosphatidylinositol and phosphatidic acid and having an average acetone insoluble content of more than 60 weight percent.

2. The adjuvant composition of claim 1 wherein Z is an alkylene oxide-containing group represented by the general formula:

$$-R^8O[(C_2H_4O)_a(C_3H_6O)_b(C_4H_8O)_c]_d-R^9$$

wherein:
$R^8$ is a linear or branched divalent hydrocarbon group of from 3 to 8 carbon atoms; $R^9$ is hydrogen, a monovalent hydrocarbon radical of from 1 to 4 carbon atoms, $R^A$—$N^\oplus$($R^{10}$)($R^{11}$)$R^{12}$$X^\ominus$, $R^B$—$N^\oplus$($R^{13}$)($R^{14}$)$R^{15}$$X^\ominus$ or $R^B$—$N^\oplus$($R^{13}$)($R^{14}$)$R^{15}$$X^\ominus$ in which $R^A$ and $R^B$ are —CH$_2$CH(OH)CH$_2$—, $R^{10}$, $R^{11}$, $R^{13}$ and $R^{14}$ are independently a monovalent hydrocarbon group of 1 or 2 carbon atoms, $R^{12}$ and $R^{15}$ are independently a linear or branched monovalent hydrocarbon group of from 1 to 6 carbon atoms and optionally substituted with one or more hydroxyl groups, and $X^\ominus$ is a $^\ominus$OC(=O)— containing group of from 2 to 22 carbon atoms; and subscript a is 1 to 15 and subscripts b and c each independently is 0 or 1 to 14 subject to the condition that a+b+c≤14, and subscript d is 0 to 1.

3. The adjuvant composition of claim 1 wherein $X^\ominus$ is represented by the general formula:

$$^\ominus OC(=O)C(R^{16})(R^{17})(R^{18})$$

in which $R^{16}$ and $R^{17}$ are independently hydrogen, hydroxyl or a monovalent hydrocarbon group of from 1 to 3 carbon atoms or hydroxymethyl, and $R^{18}$ is hydrogen, hydroxyl, a monovalent hydrocarbon group of 1 to 20 carbon atoms or a hydroxymethyl group.

4. The adjuvant composition of claim 1 wherein organosilicon surfactant (I) is present therein at 1 to 99 weight percent of the total weight of lecithin and organisilicon surfactant (I).

5. The adjuvant composition of claim 1 further comprising at least one component selected from the group consisting of foam control agent, organic solvent and water.

6. The adjuvant composition of claim 1 containing from 1 to 50 weight percent of organosilicon surfactant(s) (I) by total weight of lecithin and organosilicon surfactants (I).

7. The adjuvant composition of claim 1 containing from 1 to 10 weight percent of organosilicon surfactant(s) (I) by total weight of lecithin and organosilicon surfactants (I).

8. The adjuvant composition of claim 1 wherein the lecithin contains from 10 to 40 weight percent phosphalidylcholine.

9. An agrochemical formulation comprising an antidrift-effective amount of the adjuvant composition of claim 1.

10. The agrochemical composition of claim 9 further comprising at least one bioactive selected from the group consisting of pesticide, defoliant, fertilizer, biological, nutritional, micronutrient, growth control agent or combination thereof.

11. A method of inhibiting drift of an agrochemical formulation applied to a target area which comprises spraying the agrochemical of claim 9 within the target area.

12. A method of enhancing or increasing deposition and/or retention of spray droplets of an agrochemical formulation upon external plant tissue surfaces which comprises spraying the agrochemical formulation of claim 9 upon external plant tissue surfaces.

13. A method of enhancing or increasing penetration and/or uptake of a bioactive component of an agrochemical formulation into internal plant structures which comprises spraying the agrochemical formulation of claim 9 upon external plant tissue surfaces.

14. A method of water conditioning a plant which comprises spraying the agrochemical formulation of claim 9 upon external surfaces of the plant to be water conditioned.

15. An adjuvant composition consisting essentially of:
   a) lecithin;
   b) organosilicon surfactant of general formula (I):

$$R^1\text{—}Si(R^2)(R^3)\text{—}Z \qquad (I)$$

wherein:
   $R^1$ is a linear or branched monovalent hydrocarbon group of from 1 to 8 carbon atoms or a $R^4\text{—}Si(R^5)(R^6)\text{—}R^7\text{—}$ group in which $R^4$ is a linear or branched monovalent hydrocarbon group of from 1 to 8 carbon atoms, $R^5$ and $R^6$ are independently a linear or branched monovalent hydrocarbon group of from 1 to 4 carbon atoms and $R^7$ is a linear or branched divalent hydrocarbon group of from 1 to 4 carbon atoms;
   $R^2$ and $R^3$ are independently a linear or branched monovalent hydrocarbon group of from 1 to 4 carbon atoms; and,
   Z is an alkylene oxide-containing group of up to 15 alkylene oxide units with each unit independently containing from 1 to 4 carbon atoms; a cationic group or a quaternary group free of alkyl halide;
   c) at least one acidification agent; and
   d) at least one wetting agent;
   wherein the lecithin contains from 10 to 70 weight percent phosphalidylcholine with the balance being selected from phosphatidylethanolamine, phosphatidylinositol and phosphatidic acid and having an average acetone insoluble content of more than 60 weight percent.

16. The adjuvant composition of claim 15 wherein the lecithin contains from 10 to 40 weight percent phosphalidylcholine.

\* \* \* \* \*